(12) United States Patent
Schertiger et al.

(10) Patent No.: US 9,259,551 B2
(45) Date of Patent: Feb. 16, 2016

(54) COUPLING ARRANGEMENT FOR A TELESCOPIC DEVICE

(71) Applicant: Coloplast A/S, Humlebaek (DK)

(72) Inventors: Lars Olav Schertiger, Fredensborg (DK); Jan Torstensen, Virum (DK); Preben Luther, Birkerød (DK)

(73) Assignee: Coloplast A/S, Humlebaek (DK)

( * ) Notice: Subject to any disclaimer, the term of this patent is extended or adjusted under 35 U.S.C. 154(b) by 244 days.

(21) Appl. No.: 13/923,371

(22) Filed: Jun. 21, 2013

(65) Prior Publication Data

US 2013/0289537 A1    Oct. 31, 2013

Related U.S. Application Data

(62) Division of application No. 12/600,273, filed as application No. PCT/DK2008/050109 on May 18, 2008, now Pat. No. 8,491,568.

(60) Provisional application No. 60/924,467, filed on May 16, 2007.

(30) Foreign Application Priority Data

May 16, 2007    (DK) .................................. 2007 00736
Apr. 4, 2008     (DK) .................................. 2008 00494
May 18, 2008    (WO) ................. PCT/DK2008/050109

(51) Int. Cl.
*A61M 25/00* (2006.01)
*F16B 7/14* (2006.01)
*F16L 19/065* (2006.01)
*F16L 19/08* (2006.01)
*F16L 27/12* (2006.01)
*A61M 25/01* (2006.01)

(52) U.S. Cl.
CPC ........... *A61M 25/0017* (2013.01); *A61M 25/00* (2013.01); *F16B 7/1463* (2013.01); *F16L 19/065* (2013.01); *F16L 19/083* (2013.01); *F16L 27/12* (2013.01); *A61M 2025/0175* (2013.01); *A61M 2210/1096* (2013.01)

(58) Field of Classification Search
CPC ..... A61M 25/00; A61M 25/01; A61M 25/06; A61M 25/10; A61M 39/00; A61M 39/10; A61M 39/12; A61M 39/14; A61M 39/20
See application file for complete search history.

(56) References Cited

U.S. PATENT DOCUMENTS

2004/0163980 A1*  8/2004  Tanghoj et al. ............... 206/363

* cited by examiner

*Primary Examiner* — Melanie Hand
(74) *Attorney, Agent, or Firm* — Coloplast Corp., Coloplast A/S; Nick Baumann

(57) ABSTRACT

A telescopic device comprising a first tubular element and an extension member displaceably arranged in an axial direction within the first tubular element, wherein a coupling member is provided relatively displaceable to the extension member, between at least, a first axial position wherein the extension member is displaceable within the first tubular element, and a second axial position wherein the coupling member engages between the extension member and the first tubular element limiting displacement in at least one longitudinal direction, where the coupling member engages the interior of the first tubular element.

10 Claims, 5 Drawing Sheets

COUPLING ARRANGEMENT FOR A TELESCOPIC DEVICE

TECHNOLOGY FIELD

The present invention relates to a telescopic device and a coupling arrangement for coupling the telescopic device in an extended configuration. In particular the invention relates to a telescopic catheter and a coupling arrangement for coupling the telescopic device in a ready-to-use configuration.

BACKGROUND

The use of intermittent catheters has become almost a standard for persons not able to urinate of free will. Such users, typically paralysed persons such as para- and tetraplectics, have found that using intermittent catheters has greatly improved their freedom to move around and lead an active life as catheterisation can be performed anywhere.

However, in order for the user to come out publicly and socialise it has become more and more important that such products are discreet and easy to carry around. Thus, a demand for compact catheters, which can easily be stored and carried around in handbags or pockets, has grown.

In order to fulfil such needs, products such as the Speedi-Cath® Compact, produced by Coloplast A/S have been developed. However, this product mainly targets female users. Male users have a much longer urinary channel and thus other demands and requirements are to be fulfilled for a male product.

Many of these issues and solutions thereto have been discussed in WO 2006/045809, which discloses an expandable catheter with a transition between the individual sections allowing insertion of the transition into urethra.

However, there is still a need for alternative and improved solutions as will be discussed herein.

SUMMARY OF THE INVENTION

The present invention relates to a first tubular element and an extension member displaceably arranged in an axial direction within the first tubular element, wherein a coupling member is provided relatively displaceable to the extension member, between at least; a first axial position wherein the extension member is displaceable within the first tubular element and a second axial position wherein the coupling member engages between the extension member and the first tubular element limiting displacement in at least one longitudinal direction, where the coupling member engages the interior of the first tubular element.

It should be understood within the meaning of the present invention that the term engage can mean to interlock or cause to interlock between two parts. Furthermore, the term displace means to move from one position to another position.

It should be understood within the meaning of the present invention that the term interior can mean any part of the first tubular element, which cannot be construed as facing the exterior of the first tubular element. This may include the inner surface of the tubular element, any form of groove or extrusion on the inside of the tubular element or any surface area that is not facing the exterior or the outside of the tubular element, e.g. facing inwards and towards the central longitudinal axis of the first or the second tubular element.

It is preferred that the coupling member is palpable or cannot be felt through the walls of the first tubular element by running the fingers across the outer surface of the first tubular element. This is advantageous in that the coupling member cannot be felt and does not injure or damage anatomical structures in the body of a user when the telescopic device is inserted into the urethra of the user.

By providing a separate coupling member between the telescopic sections, i.e. the tubular element and the extension member, it has shown that the requirements relating to the production tolerances are much smaller, as the two sections do not have to fit perfectly in order for the coupling member to function properly.

It should be understood that the coupling member and the extension member are capable of relative placement in more than the first and second axial position. Thus, there may for example be many intermediate positions between the first and second axial position.

Telescopic devices may be formed of many different shapes, but typically they are formed of cylinder sections, for example catheters. Thus, in one embodiment the coupling member may be a coupling ring having an inner surface facing the extension member and an outer surface facing the first tubular element.

It should be understood that reference to outer and inner surfaces of the different elements of the invention and as described herein should be seen with respect to axis of the telescopic device. Thus, surfaces facing out and away from the axis of the telescopic device are referred to as outer surfaces, while surfaces facing inwards and towards the axis are referred to as inner surfaces.

In another embodiment, the coupling ring is expandable from a first radial extent in the first axial position to a second radial extent in the second axial position and wherein the radial extent of inner surface of the coupling ring is larger in the second radial extent than in the first radial extent. By enlarging the radial extent of the inner surface of the coupling ring, the outer surface will be pressed against the inner surface of the first tubular element, providing a tight grip. Additionally, by forming the coupling ring of a deformable and/or compressible material it is possible to achieve the frictional grip desired under many circumstances.

In one or more embodiments, the coupling ring is expandable from a first radial extent in the first axial position to a second radial extent in the second axial position and wherein the radial extent of outer surface of the coupling ring is larger in the second radial extent than in the first radial extent. By enlarging the radial extent of the outer surface of the coupling ring, the outer surface will the pressed against the inner surface of the first tubular element, providing a tight grip. It should be understood that the coupling ring can be formed of a high friction material. A high friction material should be understood as a material, which when the coupling ring is pressed against the first tubular element in its second axial position provides a high coefficient of friction. Such coefficient of friction is not absolute and may be altered for different embodiments. Thus, in one embodiment it can be above 0.1, however it could be above 0.2 or even 0.3. These values should be considered in view of the coefficient of friction between a coated catheter and the urethra, which may be as low as between 0.03 and 0.01.

This may also be considered by adapting the collapsing force, which should be understood as being the force required for pushing the extension member into the first tubular element.

Thus, it can be understood that the high friction material can be understood as a material, which would provide a collapsing force between 5-10N, in some cases.

In further embodiments of the present invention the above mentioned collapsing force may be in the range between 20-80N, where the specific size of the collapsing force may be dependent on the size and dimensions of the telescopic catheter, where catheters which have a small diameter may have less collapsing force than catheters which have a larger diameter, or vice versa. In one embodiment of the present invention the minimum collapsing force is set at 20N, such that the risk of unwanted collapse during insertion of the telescopic catheter is reduced. In another embodiment, the maximum collapsing force is achieved at 80N, such that the user may willingly collapse the telescopic catheter after use. Therefore, in a plurality of embodiments of the present invention the minimum collapsing force may be 20N and the maximum collapsing force may be 80N and the preferred collapsing force may be somewhere in-between the minimum and the maximum value, based on the specific purpose, size, dimensions or material choice of the telescopic catheter.

In yet another embodiment, the outer surface of the coupling ring can be provided with at least one rib. Such ribs provide a small contact area against the inner surface of the first tubular element, which result in a corresponding higher pressure than if the whole surface of the coupling ring distributes the pressure.

Additionally, such ribs, or the whole coupling ring can be formed of a relatively hard material compared to the first tubular element. This results in the fact that the ribs dig into, cut into or deform inwardly the inner surface of the first tubular element providing a very secure engagement.

In one embodiment, the coupling ring is formed as an open ring, having a c-shape when seen in cross section. This shape allows for the coupling ring to be easier deformed when the coupling ring is formed of a hard material as the opening in the c-shape will allow for the ring to be pressed together until the ends of the c-shape meet, providing a small enveloping circumference. Similarly, it allows for the ring to be opened, i.e. the ends of the c-shape are moved away from each other providing a large enveloping circumference.

In another embodiment, the coupling member is arranged around a conical shaped surface area of the extension member tapering along the axial direction. Thus, by sliding the coupling member along the conical shaped surface area it can, in a simple way, be moved between its first axial position and its second axial position.

In one embodiment it may be desirable to use a different material for the conical shaped surface area than that used to form the extension member in order to achieve different properties and/or for manufacturing reason. The conical shaped surface area can be provided as a separate bushing element attached to the distal end of the extension member.

In one or more embodiments of the present invention, the coupling member or coupling ring and the bushing element may be made of two different materials, as tests performed by the inventor indicate that the frictional forces between two parts constructed out of two different materials are often less than the frictional forces between two parts made out of the same material.

In one embodiment the bushing element is formed with a through-going opening along the axial direction. This for example allows for communication between passageways in the telescopic device in embodiments, wherein the extension member is a second tubular element.

Such embodiment may for example cover telescopic devices such as a telescopic intermittent urinary catheter, wherein the first tubular element can be the distal section and the second tubular element can be the proximal section. This allows urine to flow through both telescopic sections, typically from the bladder through the proximal and out through the distal section.

In one embodiment the inner surface of the first tubular element is provided with at least one protruding rim and/or at least one grove. This provides means to which the annular ribs can engage for improved coupling or if no annular ribs are provided it will function as a roughening of the surface, which also provides an improved coupling and engagement between the coupling member and the first tubular element.

BRIEF DESCRIPTION OF THE DRAWINGS

The invention will be discussed further with reference to the following example embodiments, wherein.

DETAILED DESCRIPTION

Figure 1:
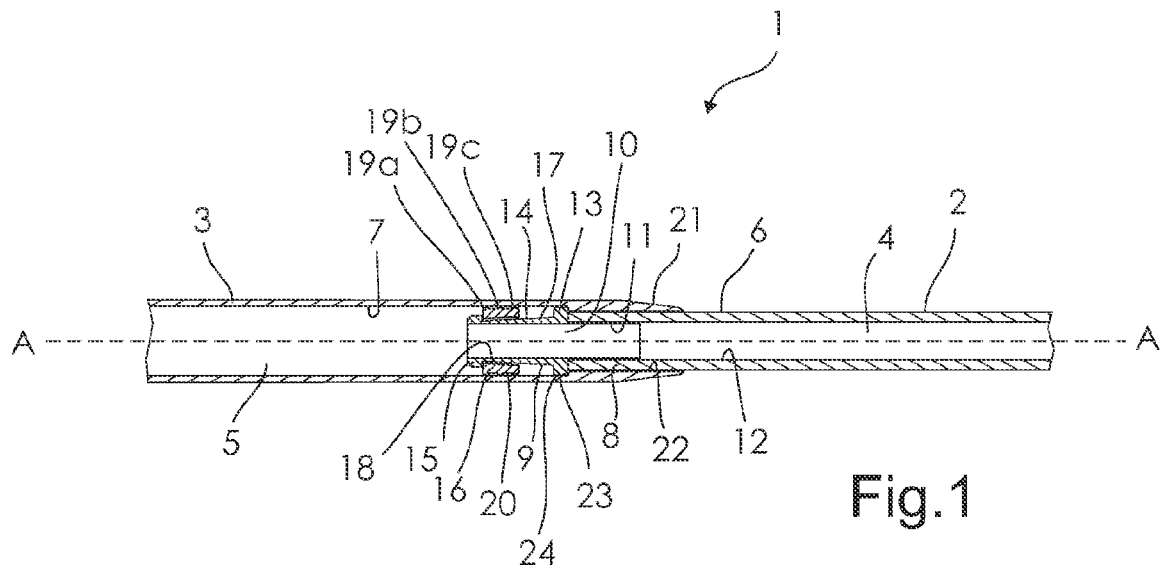
FIG. 1 shows in section the transition area between the proximal section and the distal section of a telescopic catheter according to the invention where the coupling element is in an uncoupled position.

A telescopic intermittent catheter 1 is shown partly and in section in FIG. 1 around a first axis A-A. The catheter is formed of a proximal section 2 (corresponding to the extension member described above) and a distal section 3 (corresponding to the first tubular element described above). Both sections are formed as tubular elements defining the first and second passageway 4,5 respectively, through which urine may flow in a flow direction from the first proximal section to the distal section during use.

The outer surface 6 of the proximal section 2 has a circumference, which is smaller than the circumference of the inner surface 7 of the distal section 3, so that the proximal section 2 at least partly can be displaceably placed within the second passageway 5.

At the distal end 8 of the proximal section 2, a bushing element 9 is attached.

The bushing element 9 is formed with a through-going third passageway 10 providing fluid communication between the first and second passageway 4,5. The bushing element is further formed with a neck 11 disposed within the first passageway. The neck may have a circumference slightly larger than the circumference of the inner surface 12 of the proximal section 2, thus allowing for a frictional attachment of the bushing to the proximal section. Alternatively, the neck and proximal section are glued or welded together.

The neck extends into a shoulder part in the form of a first annular rim 13. The bushing element 9 extends from the first annular rim and in the flow direction (along the axis A-A from the proximal section to the distal section) as a conical part 14, having a surface 17 that tapers from a large circumference towards a smaller circumference along the flow direction. The bushing element terminates at its distal end in a second annular rim 15.

A coupling member in the form of a coupling ring 16 is arranged around the conical part. The ring has an axial dimension of about half the axial dimension of the conical part, i.e. the length between the first annular rim and the second annular rim.

As can be seen from FIG. 1, the first annular rim has a larger radial extent than the conical part, thus providing a stop for the coupling ring in the proximal end of the conical part. The second annular rim has a larger radial extent than the conical part in the distal end, thus also functioning as a stop for the coupling ring in this end.

Therefore, when the telescopic catheter is pulled into its extended configuration, i.e. the configuration wherein it is intended to be used for catheterisation, the coupling ring abuts against the second annular rim 15 in the distal end of the conical part.

In this first axial position, the coupling ring 16 slightly presses against the inner surface 7 of the distal section, engaging slightly with the surface of the distal section. It should be understood that this slight frictional engagement is relatively small compared to the force used by a user to pull the telescopic catheter into its extended configuration. Typically, such initial engagement requires a pulling force of approximately 1-10 N. This is a relatively small pulling force, considering that a normal human being is capable of pulling with a force of 200N, corresponding to pulling 20 kg.

Such initial engagement allows the coupling ring to remain in engagement with the inner surface 7 of the distal section 3. Thus, if it is attempted to push the telescopic catheter 1 into its collapsed configuration, i.e. pushing the proximal section into the distal section the coupling ring 16 will remain in place. Thus, as can be seen from FIG. 2, the conical part 14 slides through the ring in the axial direction and the tapering surface 17 of the conical part pushes against the inner surface 18 of the coupling ring 16, pushing the coupling ring into its second axial position. This creates a tight engagement between the bushing element 9 and the distal section 3.

As can be understood, a high frictional engagement is desired between the outer surface of the coupling ring and the inner surface of the distal section, when the coupling ring is in its second axial position. However, a relatively smaller frictional engagement may be desired between the inner surface of the coupling ring and the surface of the conical part. Thus, the coupling ring may slide over the surface of the conical part while engaged with the inner surface of the distal section. Forming the bushing element in e.g. polyamid or Teflon may provide such a relative low frictional engagement.

Thus, in one alternative embodiment (not shown) the coupling ring may be formed of two materials; An inner material forming the inner surface of the coupling ring providing a relatively low frictional engagement with the surface of the conical part; and an outer material forming the outer surface of the coupling ring providing a relatively high frictional engagement with the inner surface of the distal section.

In order to further provide a tight engagement in the second axial position of the coupling ring, the coupling ring may be provided with at least one annular rib 19, in the embodiment shown there are provided three annular ribs 19a, 19b, 19c on the outer surface 20 of the coupling ring. This provides a small contact area with the inner surface of the distal section. Thus, pressure will be distributed through these relatively small contact areas, which results in a high pressure distribution through each rib whereby the ribs have a tendency to dig into the material of the distal section providing a gripping engagement between the locking ring 16 and the distal section 3.

Although such tight engagement is relative and depends on the intended use of the telescopic catheter, it should be understood that the force required to pull the telescopic catheter from a collapsed configuration, often the configuration wherein the catheter is stored, to its extended configuration, wherein it is intended to be used, is much smaller than pushing the catheter from its extended configuration towards its collapsed configuration.

Figure 2:
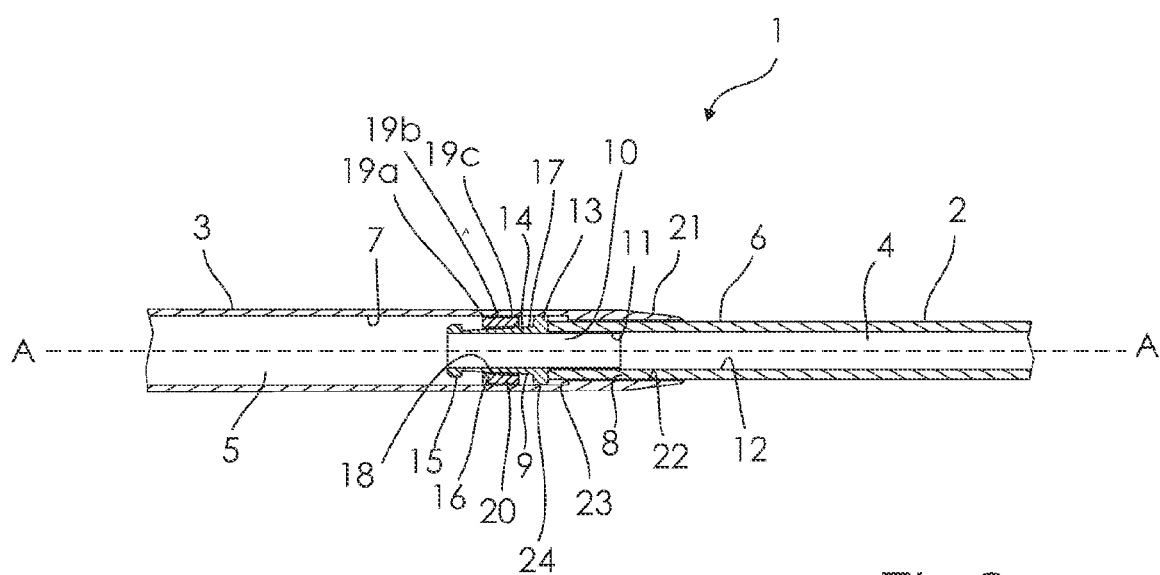
FIG. 2 shows in section the transition area between the proximal section and the distal section of a telescopic catheter according to the invention where the coupling element is in a coupled position.

Furthermore, as can be seen in both FIGS. 1 and 2, the distal section 3 is at its proximal end 21 formed with a narrow inner surface part 22 having a decreased inner circumference compared to the circumference of the inner surface 7, i.e. the rest of the distal section 3. This provides an edge 23, provided in the transition between the inner surface 7 and the narrowed inner surface part 22. The edge 23 functions as a stop against the first annular flange 13, providing that the outer circumference 24 of the first annular flange is greater than the inner circumference of the narrowed inner surface part 22. This prevents that the proximal section and the distal section are pulled apart unintentionally.

Figure 3:
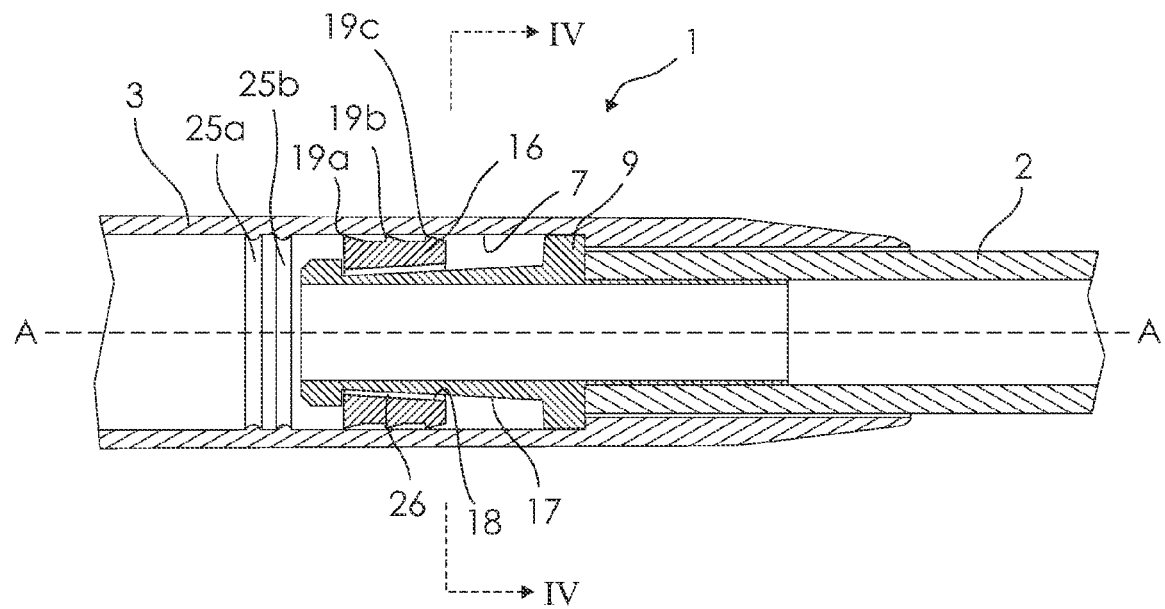
FIG. 3 shows in section the transition area between the proximal section and the distal section of a telescopic catheter according to the invention where the coupling element is in an uncoupled position.

FIG. 3 shows in section the transition area between the proximal section 2 and the distal section 3 of a telescopic catheter 1 where the coupling ring 16 is in its initial engagement state. The size of the radial circumference of the coupling ring 16 is slightly larger than the radial circumference of the inner surface 7 of the distal section 3, in a way that the annular ribs 19a, 19b, 19c of the coupling ring 16 are in continuous contact with the inner surface 7 of the distal section 3, providing frictional engagement between the coupling ring 16 and the inner surface 7. This means that when the proximal section 2 and the distal section 3 of the telescopic catheter 1 are manoeuvred from their collapsed position to their extended position, the coupling ring is in continuous contact with the inner surface 7 during the transition, while being held in place relative to the bushing element 9 of the proximal section 2 by the second annular rim 15.

Figures 4A, 4B:
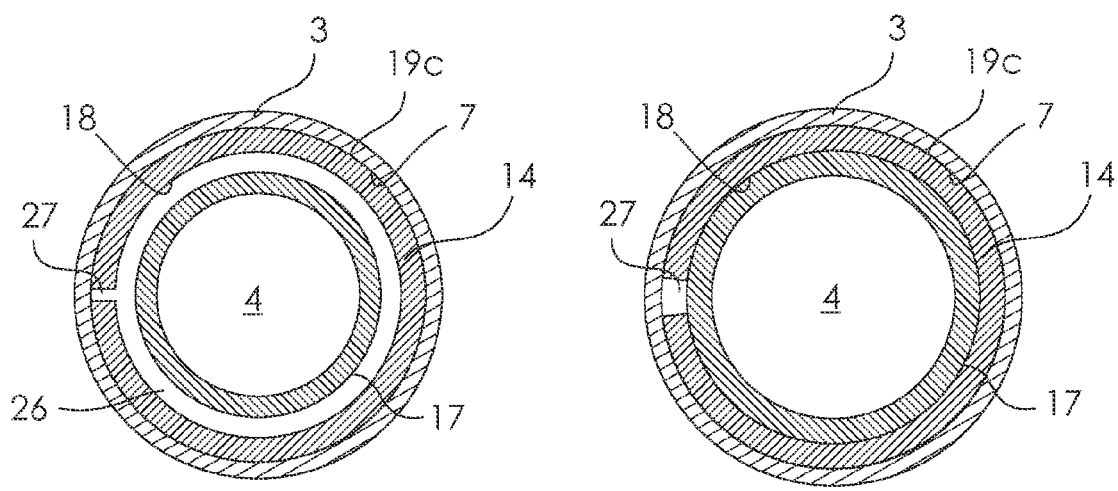
FIGS. 4a and 4b show a section of a catheter according to the present invention taken along line IV-IV.

In this embodiment of the present invention, as shown in FIG. 3, the coupling ring 16 is in contact with the second annular rim 15 and there is a slit 26 between the inner surface 18 of the coupling ring 16 and the tapering surface 17 of the conical part 14, which extends along the radial inner surface 18 of the coupling ring, as shown in FIG. 4a, which ensures that the conical part 14 of the bushing element 9 may be pushed a short distance into the coupling ring 16 without providing full contact between the inner surface 18 and the tapering surface 17. The coupling ring 16 in full contact between the inner surface 18 and the tapering surface 17 is shown in FIG. 4b, where the slit has been filled and the opening 27 in the coupling ring has been widened, as the annular rib 19c is pressed into the inner surface 7 of the distal section 3.

In order to ensure that the coupling ring 16 maintains its axial position when the proximal part 2 is pushed towards its collapsed position and the conical part 14 is moved relative to the coupling ring 16, it is important that the frictional forces $F_1$ between the annular ribs 19a, 19b, 19c and the internal surface 7 of the distal section 3 are larger than the frictional forces $F_2$ between the inner surface 18 of the coupling ring 16 and the tapering surface 17 of the conical part 14, $F_1 > F_2$. In some embodiments of the present invention it is advantageous that $F_1$ is significantly larger than $F_2$, $F_1 >> F_2$. I Preferably F1 is in the range 2-100% larger than F2, more preferably F1 is in the range 5-70% larger than F2, yet more preferably F1 is in the range 10-40% larger than F2, and most preferably F1 is approximately 20% larger than F2. The preferred ratio between F1 and F2 is based on the specific construction of the catheter and the specific percentage may vary from one embodiment to another embodiment of the present invention.

In the context of the present invention, the term frictional force means the force of two surfaces in contact. The term may be understood as either static friction, i.e. friction between two objects, which are not moving relative to each other, or kinetic (dynamic) friction, which is the friction between two objects moving relative to each other. The frictional forces between the annular ribs 19a. 19b, 19c and the inner surface 7 of the distal section 3 are considered as static friction, whereas the frictional forces between the inner surface 18 of the coupling ring 16 and the tapering surface 17 of the conical part 14 are considered as kinetic friction. A more detailed definition of friction may be seen in Physics for Scientists and Engineers with modern Physics, Fifth Edition, Serway and Beichner, Sounders College Publishing, ISBN 0-03-022657-0.

In one embodiment of the present invention, the force $F_1$ is increased by providing the coupling ring with at least one annular rib 19, which provides a smaller contact surface between the coupling ring 16 and the inner surface 7 of the distal section 3 and ensures that the forces in the radial direction are distributed over a small surface area on the inner surface 7. Furthermore, this ensures that the annular ribs 19 are capable of digging into the inner surface 7, providing increased frictional forces. The friction F1, could in different embodiments be increased by roughening the outer surface of the coupling part 16, or by providing the outer surface with treads, similar to those found on tires to increase traction. Different methods of increasing the frictional force $F_1$ would be obvious to the skilled person based on the present invention.

As mentioned earlier, it is important to minimize the frictional force F2 between the inner surface 18 of the coupling ring 16 and the tapered surface 17 of the conical part 14. This may be achieved by constructing the inner surface 18 of the coupling ring 16 and/or the tapered surface 17 of the conical part 14 of low friction material, such as nylon, or by coating the surfaces 17,18 with a non-stick material such as Teflon or similar material. Furthermore, the low friction surface area may be obtained by polishing the surfaces to a glossy finish, such that any roughness of the surfaces may be removed, minimizing the friction. Even further, the conical part 14 and the coupling ring may be completely untreated after fabrication where the construction of the conical part 14 and the coupling ring 16 may provide a suitable balance between the frictional forces, $F_1 > F_2$.

In another embodiment, the inner surface of the coupling ring and the tapered surface of the conical part may be lubricated with a high viscous substance, such as grease, oil or similar substances, where it would be important to ensure that the substance could not come in contact with the contact surface between the inner surface 7 of the distal section 3 and the outer surface 19 of the coupling ring 16.

The particular embodiment of the present invention, as shown in FIG. 3 is provided with two rims 25a and 25b, which the coupling ring 16 may easily pass when the proximal section 2 is pulled towards the extended position of the telescopic catheter 1. The rims 25a and 25b, provide a redundant securing means, which ensures that the coupling ring does not slide past the first 25a or the second rim 25b, if the frictional forces or the gripping engagement between the annular ribs 19a, 19b, 19c and the inner surface 7 of the distal section 3 are less than the force pushing the coupling ring 16 towards the proximal end of the distal section 3, when the proximal section 2 is being pushed into its collapsed configuration.

Figure 5:
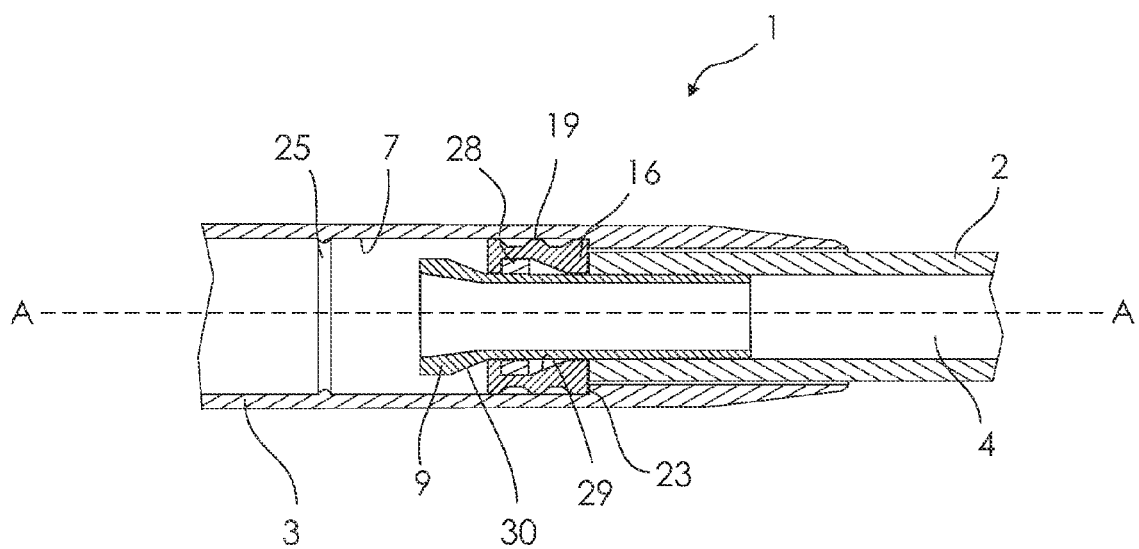
FIG. 5 shows in section the transition area between the proximal section and the distal section of one embodiment of a telescopic catheter according to the invention where the coupling element is in an uncoupled position.
Figure 6:
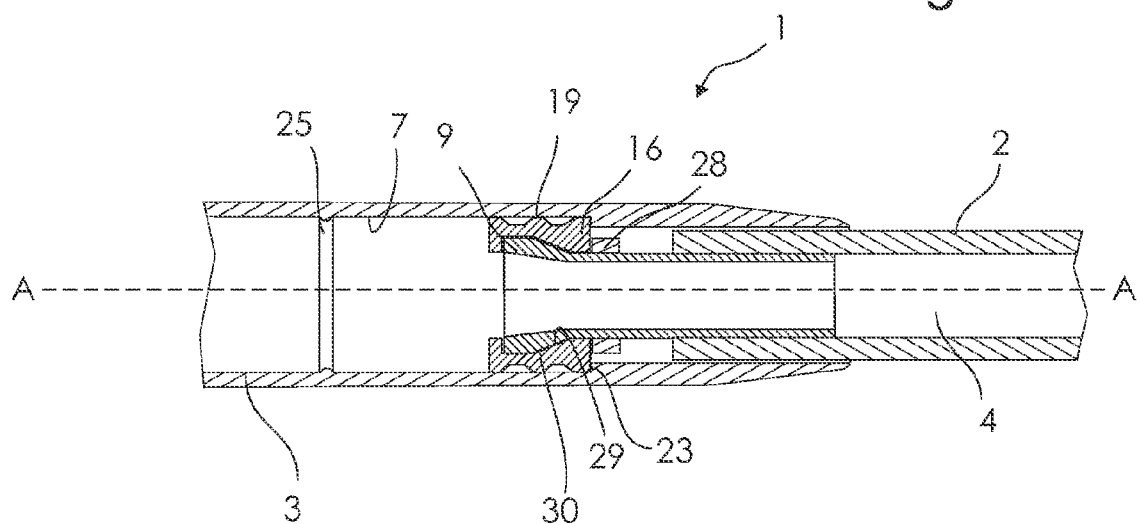
FIG. 6 shows in section the same where the coupling element is in a coupled position, FIG. 7a and /b shows a section of a telescopic catheter, where one surface is provided with longitudinal grooves.

Another embodiment of the present invention is shown in FIG. 5 and FIG. 6, where a telescopic catheter 1, having a proximal section 2 and a distal section 3 in an extended position. FIG. 5 shows the proximal section 3 in an unlocked position, where the coupling ring 16 is not fully engaged into the inner surface 7 of the distal member 3 and the proximal section 2 may still be moved in a direction towards its collapsed position. In order to lock the proximal section 2 in its extended position, the proximal section 2 has to be pulled further towards its extended position in a way that the bushing element 9 expands the c-shaped coupling ring 16, by means of the tapered outer surface 30 of the bushing 9 and the tapered inner surface 29 of the coupling ring 16 and the structural element 28. The coupling ring 16 is held in its position by means of the edge 23, which stops the coupling ring 16 from moving in the direction of the extended proximal section 2.

The telescopic catheter 1 in its locked position is shown in FIG. 6, where the distal section of the bushing element 9 is snugly fit inside the coupling ring 16, where the tapered outer surface 30 of the bushing element borders on the inner surface 29 of the coupling ring 16 and the structural element 28 and the distal edge of the bushing element 9 prevents the bushing element in exiting the inside of the coupling ring 16 in a direction towards its collapsed position. As the bushing element 9 is positioned inside the coupling ring 16, the coupling ring is expanded from its normal circumference, as shown in FIG. 5, into an expanded outer circumference, reinforced by the bushing element 9, where the external surface 19 of the coupling ring is fully engaged into the inner surface 7 of the distal member 3. The fully engaged coupling ring 16 ensures that the proximal section 2 is limited in displacement in a direction towards the telescopic catheter's 1 collapsed position.

Figure 7A:
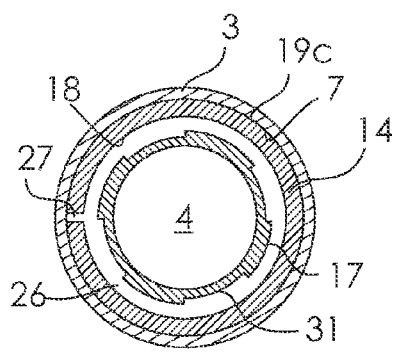
Figure 7B:
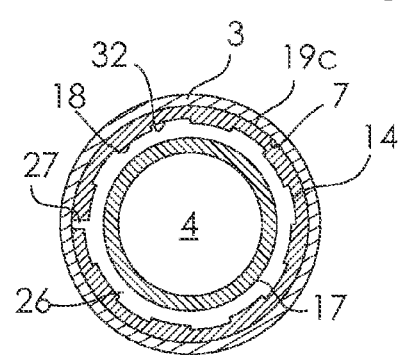

Another embodiment of the present invention is shown in FIG. 7a where the tapered surface 17 is provided with a plurality of longitudinal grooves 31 in a direction parallel to the axis A, the axis A is shown in FIG. 6. The longitudinal grooves 31 decrease the surface area of the tapered surface 17 compared to a uniform surface, such that there is less area of the tapered surface 17 that comes in contact with the inner surface 18 of the coupling ring 16. An alternative embodiment is shown in FIG. 7b, where the inner surface 18 of the coupling ring 16 has been provided with longitudinal grooves 32 in a direction parallel to the axis A. The longitudinal grooves 32 decrease the surface area of the inner surface 18 of the coupling ring 16 compared to a uniform surface area. This means that the contact surface between the tapered surface 17 and the inner surface 18 of the coupling ring 16 is less than with a uniformed surface and the kinetic friction between the surfaces is reduced.

Figure 8:
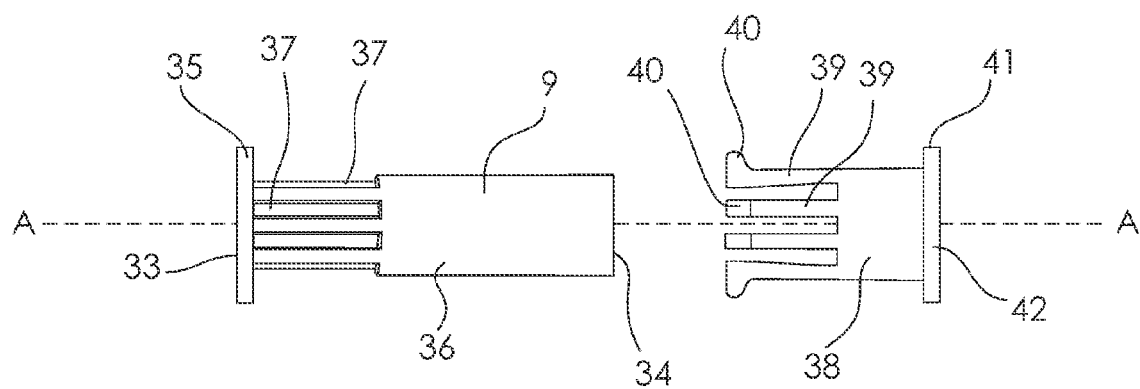
FIG. 8 shows a side view of a bushing element and a coupling ring according to the present invention.
Figure 9:
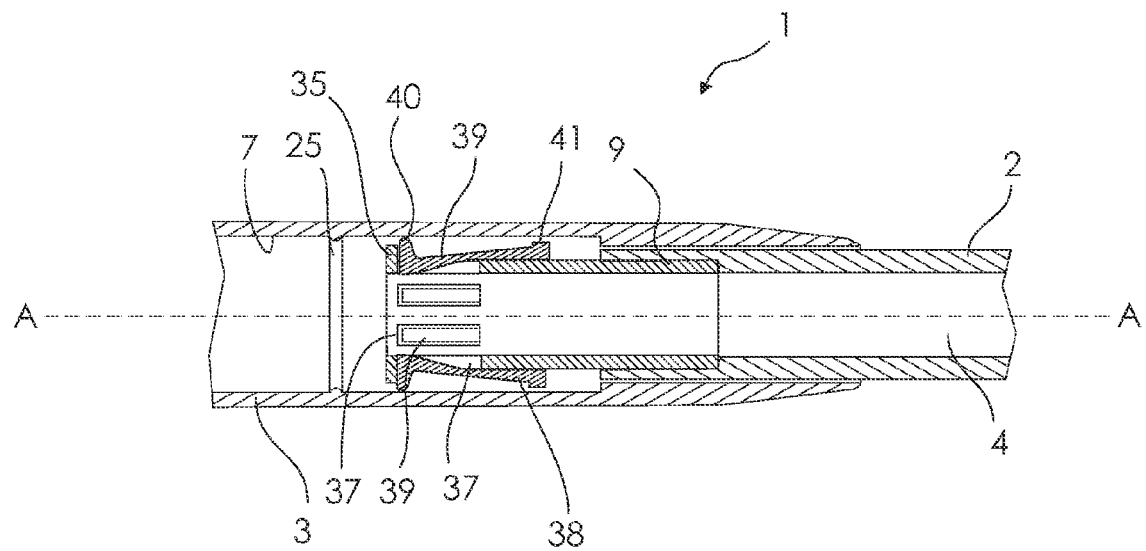
FIG. 9 shows in section the transition area between the proximal section and the distal section of another embodiment of a telescopic catheter, having the bushing element and coupling ring of FIG. 8, where the coupling element is in a coupled position.

FIG. 8 shows another embodiment of the present invention, where the bushing element 9 has a uniform cylindrical form from the distal end 33 to the proximal end 34. At the distal end 33 there is provided a collar 35, which extends radially away from the central longitudinal axis of the bushing element 9. At the proximal end 34 of the bushing element 9, the bushing element is connected to the proximal section 2 of the catheter 1, as shown in FIG. 9. The outer surface 36 of the bushing element 9 is provided with a plurality of through going openings 37, which are in this embodiment larger in the direction parallel to the central axis A, than along the radial curvature of the of the outer surface 36. A coupling ring 38 is moveably arranged onto the outer surface 36 of the bushing element 9, where a plurality of arms 39, each arm 39 having at least one projection, extending in a direction radially away from the central axis A. The arms are arranged to be resiliently moveable in a radial direction from the central axis A. The arms 39 are arranged to slot into the through going openings 37 of the bushing element 9, such that at least one arm 39 slots into one opening 37. The coupling ring 38, is provided with a collar 41, which extends radially away from the central axis A. The projections 40 of the arms 39 are arranged to extend at least the same radial distance from the axis A as the outer surface 42 of the collar 41 and in one embodiment the projections 40 extend further in a radial distance from the axis A than the outer surface 42.

FIG. 9 shows a sectional view of a catheter 1 according to the present invention in an unlocked position, where the catheter is provided with the bushing element 9 and the coupling ring 38 as shown in FIG. 8. In an unlocked position the projections 40 of the arms 39 of the coupling ring 38 are in contact with the inner surface 7 of the distal section 3. The contact between the coupling ring 38 and the inner surface 7 ensures that there is friction between them. As the proximal section is pulled into the catheters 1 extended position, the collar 35 of the bushing element 9, ensures that the coupling ring 38 does not slide off the bushing element 9.

Figure 10:
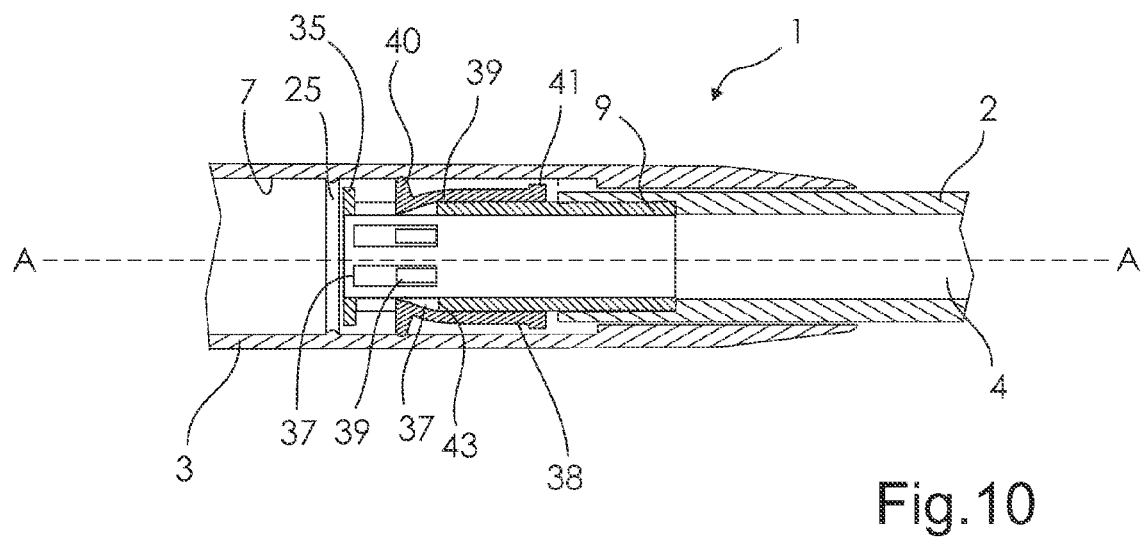
FIG. 10 shows in section the same where the coupling element is in a coupled position.

FIG. 10. shows a sectional view of the catheter, as shown in FIG. 9, in a locked position. The proximal section 2 has been manoeuvred towards the catheter's 1 collapsed configuration and the bushing element 9 has moved relative to the distal section 3 and the coupling ring 38. The proximal edge 43 of the through going opening 37 presses against the resilient arm 39, pressing the arm outwardly in a radial direction away from the central axis A, such that the projection 40 presses into the inner surface 7 of the distal section 3. The same pressure is exerted to all of the plurality of arms of the coupling ring and consequently to all of the plurality of projections 40. The pressure exerted onto the arm locks the proximal section 2 in an extended position and ensures that the catheter 1 may be inserted into a urethra of a user of the catheter, without risking an unwanted collapse of the catheter.

In the previously mentioned embodiment, it is important that the frictional force between the inner surface 7 of the distal section and the outer surface of the coupling ring is larger than the frictional force between the inner surface of the coupling ring and the outer surface of the bushing element, ensuring that the bushing element is displaceable relative to the coupling ring, when manoeuvring the catheter into its locked configuration.

Figure 11:
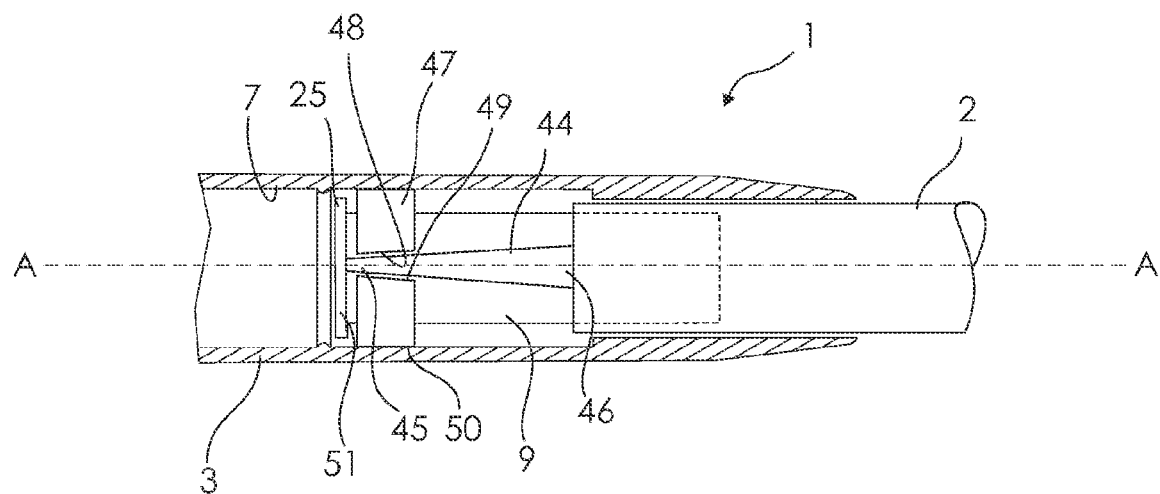
FIG. 11 shows in section the transition area between the proximal section and the distal section of yet another embodiment of a telescopic catheter according to the invention where the coupling element is in an uncoupled position.
Figure 12:
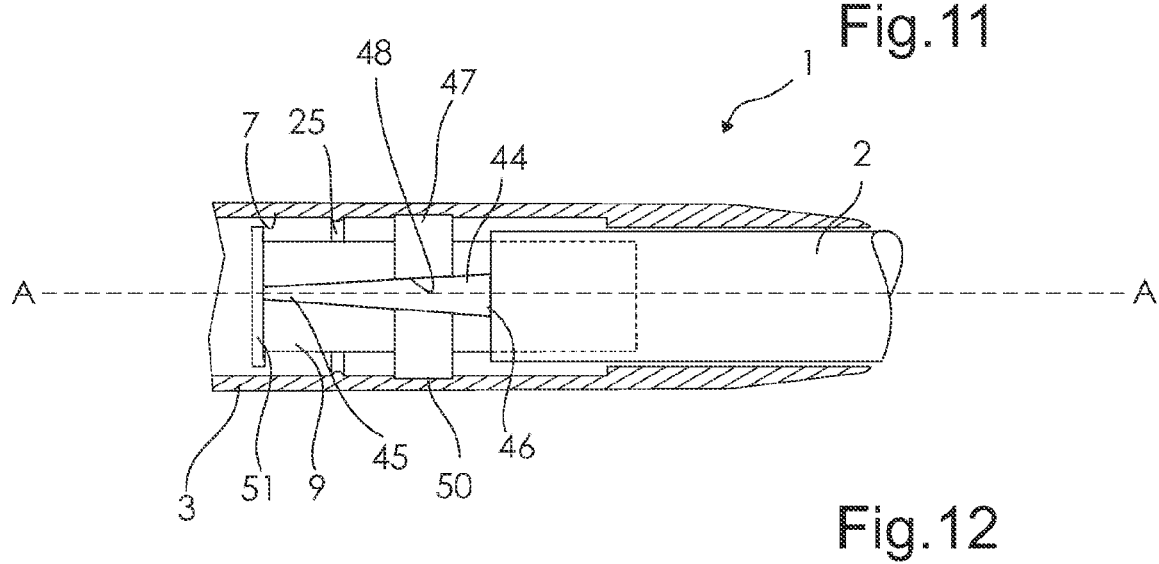
FIG. 12 shows in section the same where the coupling element is in a coupled position.

FIG. 11 and FIG. 12 show a partial sectional diagram of another embodiment of a telescopic catheter according to the present invention in an unlocked position. In this embodiment the bushing element 9 is of a uniform cylindrical shape and is provided with an expansion means 44, in the form of a wedge shaped element. The central axis of the expansion means 44 is positioned in a direction that is parallel to the central axis A of the catheter 1, having a distal end 45, which is pointed and a proximal end 46 which is wide. The catheter 1 is provided with an open coupling ring 47, which is substantially c-shaped, where the expansion means 44 are positioned within the opening 48 of the coupling ring. The free ends 49 of the coupling ring 47 are substantially parallel to the sides of the expansion means 44. The contact surface between the coupling ring 47 and the bushing element 9, is preferably a low friction surface, such that the coupling ring 47 can easily be manoeuvred relative to the bushing element 9. The outer surface 49 of the coupling ring 47 is in contact with the inner surface 7 of the distal section 3 of the catheter 1, where the frictional forces between the inner surface 7 and the outer surface 50 of the coupling ring is to be larger that the frictional forces between the inner surface 48 of the coupling ring 47 and the bushing element 9.

The proximal section 2 has been manoeuvred into its extended position and a collar 51 on the distal end of the bushing element 9 ensures that the coupling ring 47 does not slide of the bushing element 9. In order to lock the catheter 1 and the proximal section 2 in the catheters 1 extended position, as shown in FIG. 12, the proximal section 2 is manoeuvred towards its collapsed position, as mentioned earlier and the bushing means 9 move relative to the coupling ring 47, where the expansion means 44 engage the opening 48 of the coupling ring 47 and force the coupling ring 47 to expand in a radial direction away from the central axis A. The expanded coupling ring 47 engages the inner surface 7 of the distal section 3 and ensures that the proximal section 2 of the catheter 1 remains in its extended position, such that the extended catheter 1 can be inserted into the urethra of the user.

As can be understood from the above, one way of determining the force required to pull the catheter into an extended configuration or the force required to push the catheter into a collapsed configuration may be through the materials used for the different part of the catheter.

Thus, the proximal section may be produced of rather soft materials such as polyurethane, PVC (polyvinylchloride) or similar flexible materials and the distal section may for example be produced of hard materials such as polyurethane, polyolefines, PEEK (polyetheretherketon), PC (polycarbonate), PET (polyester, polyethylenephtalate), ABS (acrylonitril-butadien-styrene) and/or MABS (methylmethacrylate acrylonitril-butadien-styrene). As can be seen some materials, for example polyurethane, can be used for both the distal and proximal section, although with different hardness.

The bushing element is typically formed of a relatively hard material in order to prevent deformation of the conical shaped surface area when the coupling ring presses against the distal section in its second axial position. Such materials can be numerous and selected between many different plastics but also aluminium, steel, brass etc. In order to be able to weld the bushing element to the proximal section a polyurethane may be used, for example Desmopan as mentioned above. Other plastic materials can for example be polyolefins, such as polypropylene, polyethylene, EVA (polyethylene vinylacetate copolymer), ABS MABS, Kraton, PET, PC, PCTG(copolyester/polycarbonat) blends, HIPS (high impact polystyrene), PA (polyamid), SAN (styrene-acrylonitril), PS (polystyrene) and SEBS (styrene-ethylene/bothylene-styrene).

In one or more embodiments of the present invention, the coupling ring and the distal section may be manufactured of the same type of material, such as those materials described above in relation to the coupling ring and the distal section.

As mentioned previously, the coupling ring may be formed relatively hard relative to the distal section in order to be able to dig into the material of the distal section. Or, if the coupling ring is formed relatively soft relative to the distal section it is possible to provide a frictional engagement. In such embodiment, the coupling ring can for example be formed of SBS (Styrene Butadiene Styrene), SEBS, silicone, TPU (Thermoplastic Urethane), rubber (such as nitril, santoprene etc.).

Coupling rings formed of a relatively hard material may be formed as open rings, i.e. having a c-shape when seen in cross section. This allows for the ring to have spring like characteristics where it can be compressed into a smaller annular enveloping circumference and expanded to a larger annular enveloping circumference than when the open ring is in its neutral, non-loaded, shape.

Coupling rings formed of a relatively soft material may be formed as closed ring, as the material itself is being compressed providing a frictional engagement as described above.

Furthermore, the inner surface of the distal section can be formed with rims and/or groves. These ribs or groves provide an even firmer engagement between the coupling ring and the distal section, as the annular ribs formed on the outer surface of the coupling ring will engage with the ribs or groves. Such ribs or groves can be formed at the proximal end of the distal section in order to improve the engagement between the distal section and the proximal section when the telescopic catheter is in its expanded configuration.

The invention claimed is:

1. A telescopic intermittent urinary catheter comprising a distal section and a proximal section displaceably arranged in an axial direction within the distal section, wherein a coupling member is provided relatively displaceable to the proximal section, between at least,
   a first axial position wherein the proximal section is displaceable within the distal section, and
   a second axial position wherein the coupling member engages between the proximal section and the distal section limiting displacement in at least one longitudinal direction,
   where the coupling member engages the interior of the distal section,
   wherein the coupling member is arranged around a conical shaped surface area of the proximal section tapering along the axial direction and engages an inner surface of the distal section.

2. The catheter of claim 1, wherein the coupling member is a coupling ring having an inner surface facing the proximal section and an outer surface facing the distal section.

3. The catheter of claim 2, wherein the coupling ring is expandable from a first radial extent in the first axial position to a second radial extent in the second axial position and wherein the radial extent of the inner and/or the outer surface of the coupling ring is larger in the second radial extent than in the first radial extent.

4. The catheter of claim 2, wherein the coupling ring is formed as an open ring, having a c-shape when seen in cross section.

5. The catheter of claim 1, wherein the outer surface of the coupling member is provided with at least one rib.

6. The catheter of claim 1, wherein the conical shaped surface area is provided as a separate bushing element attached to the distal end of the proximal section.

7. The catheter of claim 6, wherein the bushing element is formed with a through-going opening along the axial direction.

8. The catheter of claim 1, wherein the conical shaped surface area is provided with a low friction surface.

9. The catheter of claim 2, wherein a frictional force, F1, between the inner surface of the distal section and the outer surface of the coupling member is larger than a frictional force, F2, between the inner surface of the coupling member and the proximal section.

10. A telescopic intermittent urinary catheter comprising:
    a distal section;
    a proximal section disposed in an axial direction within the distal section; and
    a coupling member disposed on a conical surface of the proximal section and engaged with an interior surface of the distal section, where the conical surface is tapered in the axial direction;
    wherein the coupling member is configured to engage between the proximal section and the distal section to limit movement of the proximal section into the distal section.

* * * * *